(12) United States Patent
Hostetler et al.

(10) Patent No.: US 8,101,745 B2
(45) Date of Patent: Jan. 24, 2012

(54) LUNG-TARGETED DRUGS

(75) Inventors: Karl Y. Hostetler, Del Mar, CA (US); James R. Beadle, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 943 days.

(21) Appl. No.: 11/793,276

(22) PCT Filed: Dec. 15, 2005

(86) PCT No.: PCT/US2005/045579
§ 371 (c)(1), (2), (4) Date: Apr. 25, 2008

(87) PCT Pub. No.: WO2006/066074
PCT Pub. Date: Jun. 22, 2006

(65) Prior Publication Data
US 2008/0221061 A1 Sep. 11, 2008

Related U.S. Application Data

(60) Provisional application No. 60/637,195, filed on Dec. 16, 2004.

(51) Int. Cl.
C07H 19/06 (2006.01)
C07H 19/16 (2006.01)
(52) U.S. Cl. ............ 536/26.1; 536/26.7; 536/26.8
(58) Field of Classification Search .......... 536/26.1, 536/26.7, 26.8
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,328,245 A | 5/1982 | Yu et al. | |
| 4,409,239 A | 10/1983 | Yu | |
| 4,410,545 A | 10/1983 | Yu et al. | |
| 4,522,811 A | 6/1985 | Eppstein et al. | |
| 4,659,825 A | 4/1987 | Holy et al. | |
| 4,724,233 A | 2/1988 | De Clercq et al. | |
| 4,808,716 A | 2/1989 | Holy et al. | |
| 5,033,352 A | 7/1991 | Kellogg et al. | |
| 5,052,558 A | 10/1991 | Carter | |
| 5,059,595 A | 10/1991 | Le Grazie | |
| 5,073,543 A | 12/1991 | Marshall et al. | |
| 5,120,548 A | 6/1992 | McClelland et al. | |
| 5,323,907 A | 6/1994 | Kalvelage | |
| 5,354,556 A | 10/1994 | Sparks et al. | |
| 5,484,809 A * | 1/1996 | Hostetler et al. ........... 514/449 |
| 5,532,225 A | 7/1996 | Reist et al. | |
| 5,571,534 A | 11/1996 | Jalonen et al. | |
| 5,591,767 A | 1/1997 | Mohr et al. | |
| 5,639,476 A | 6/1997 | Oshlack et al. | |
| 5,641,763 A | 6/1997 | Holy et al. | |
| 5,650,520 A | 7/1997 | Hao et al. | |
| 5,656,745 A | 8/1997 | Bischofberger et al. | |
| 5,674,533 A | 10/1997 | Santus et al. | |
| 5,717,095 A | 2/1998 | Arimilli et al. | |
| 5,733,566 A | 3/1998 | Lewis | |
| 5,733,896 A | 3/1998 | Holy et al. | |
| 5,798,340 A | 8/1998 | Bischofberger et al. | |
| 5,817,647 A | 10/1998 | Casara et al. | |
| 5,827,831 A * | 10/1998 | Hostetler et al. ........... 514/47 |
| 5,840,716 A | 11/1998 | Ubasawa et al. | |
| 5,854,228 A | 12/1998 | Webb, II et al. | |
| 5,869,467 A | 2/1999 | Holy et al. | |
| 5,877,166 A | 3/1999 | Reist et al. | |
| 5,886,179 A | 3/1999 | Arimilli et al. | |
| 5,922,696 A | 7/1999 | Casara et al. | |
| 5,955,610 A | 9/1999 | Nguyen-Ba et al. | |
| 5,977,061 A | 11/1999 | Holy et al. | |
| 6,005,107 A | 12/1999 | Nguyen-Ba et al. | |
| 6,057,305 A | 5/2000 | Holy et al. | |
| 6,127,540 A | 10/2000 | Nguyen-Ba et al. | |
| 6,197,775 B1 | 3/2001 | Ubasawa et al. | |
| 6,225,460 B1 | 5/2001 | Bischofberger et al. | |
| 6,350,458 B1 | 2/2002 | Modi | |
| 6,444,656 B1 | 9/2002 | Nguyen-Ba et al. | |
| 6,455,571 B1 | 9/2002 | Maring et al. | |
| 6,562,861 B1 | 5/2003 | Babu et al. | |
| 6,653,296 B1 | 11/2003 | Holy et al. | |
| 2003/0109498 A1 | 6/2003 | Yuasa et al. | |
| 2004/0023921 A1 | 2/2004 | Hong et al. | |

(Continued)

FOREIGN PATENT DOCUMENTS
CS        263953        5/1988
(Continued)

OTHER PUBLICATIONS

FDA Guidance for Industry: Container Closure Systems for Packaging Human Drugs and Biologics (May 1999).*
Bronson et al. J. Med. Chem., 1989, 32, p. 1457-1463.*
Bronson et al. Nucleotide Analogues as Antiviral Agents, chapter 5, p. 72-87, ACS Symposium Series, 1989, vol. 401.*
Hostetler et al. Antiviral Research, 2007, 73(3), p. 212-218.*
Alexander, et al., J. Med. Chem. 46, 4205-4208, 2003.
Baker, et al., Antiviral Res. 57: 13-23, 2003.
Buchwald, et al., Surgery 88:507, 1980.
Buller, et al., Virology, 318:474-481, 2004.
Chand, P., Expert Opinion on Therapeutic Patents, 15 (8),1009-1025, 2005.
Cundy, K.C., Clinical Pharmacokinetics, 36:127-143, 1999.
De Clercq, Clinical Microbiology Reviews, 14:382-297, 2001.
Hostetler, et al., Antiviral Research, 31:59-67, 1996.
Huggins, et al., Antiviral Research, 53:A66 (104), 2002.

(Continued)

*Primary Examiner* — Shaojia Anna Jiang
*Assistant Examiner* — Jonathan S Lau
(74) *Attorney, Agent, or Firm* — Kilpatrick Townsend & Stockton LLP (57) ABSTRACT

Methods and compositions are provided for treating lung diseases, including but not limited to infections and small cell and non-small cell lung cancer, by conjugating a drug of interest to glycerol ethers or glycerol phosphate ethers.

3 Claims, 2 Drawing Sheets

U.S. PATENT DOCUMENTS

2004/0023928 A1    2/2004    Colacino

FOREIGN PATENT DOCUMENTS

| | | |
|---|---|---|
| CS | 263955 | 5/1988 |
| CS | 263956 | 5/1988 |
| CS | 292199 | 10/2002 |
| EP | 0 262 876 | 9/1987 |
| RU | 2187509 | 8/2002 |
| WO | WO 91/19726 | 12/1991 |
| WO | WO 92/03462 | 3/1992 |
| WO | WO 92/07065 | 4/1992 |
| WO | WO 93/15187 | 8/1993 |
| WO | WO 93/19075 | 9/1993 |
| WO | WO 95/32984 | 12/1995 |
| WO | WO 96/39831 | 12/1996 |
| WO | WO 98/38202 | 9/1998 |
| WO | WO 98/42351 | 10/1998 |
| WO | WO 99/62921 | 12/1999 |
| WO | WO 00/29414 | 5/2000 |
| WO | WO 01/39724 | 6/2001 |
| WO | WO 01/64693 | 9/2001 |
| WO | WO 02/057288 | 7/2002 |
| WO | WO 02/087465 | 11/2002 |
| WO | WO 03/002580 | 1/2003 |
| WO | WO 03/050129 | 6/2003 |
| WO | WO 03/090690 | 11/2003 |
| WO | WO 03/090691 | 11/2003 |
| WO | WO 03/099294 | 12/2003 |
| WO | WO 2004/096286 | 11/2004 |

OTHER PUBLICATIONS

Keith, et al., *Antimicrobial Agents and Chemotherapy*, 48:5, p. 1869-1871, May 2004.
Kern, et al., Antimicrobial Agents Chemotherapy, 46:991-995, 2002.
Maloisel, et al., Antiviral Chemistry and Chemotherapy I, 10:333-345, 1999.
Quenelle, Antimicrobial Agents Chemotherapy, 48:404-412, 2004.
Saudek, et al., N. Engl.J.Med. 321:574, 1989.
Sefton, CRC Crit. Ref. Biomed. Eng. 14:201, 1987.

\* cited by examiner

LUNG-TARGETED DRUGS

RELATED APPLICATIONS

This application is a §371 of PCT/US2005/045579, filed Dec. 15, 2005, which claims priority to U.S. Provisional Patent Application No. 60/637,195, filed Dec. 16, 2004, entitled "Lung-Targeted Drugs." The disclosure of the above-referenced applications is incorporated by reference herein in its entirety.

FIELD

Provided herein are conjugates, compositions and methods for targeting certain drugs to lung. The conjugates provided are used in methods for treatment of lung infections and lung cancers. In certain embodiments, the compounds provided herein are conjugates of drugs with glycerol ethers.

BACKGROUND

Anticancer and antimicrobial drugs do not target the organ of interest when given orally. For example, in lung cancer and various pulmonary infections, it has not been possible to target oral drugs to the site of disease. For example, cidofovir has been identified as an active antiviral against vaccinia and smallpox (De Clercq, Clinical Microbiology Reviews, 14:382-397, 2001 and Baker et al., Antiviral Res. 57: 13-23, 2003.) but it is not orally active (Cundy K. C., Clinical Pharmacokinetics, 36:127-143, 1999). However, alkoxyalkyl esters of cidofovir (CDV) were orally active and several orders of magnitude more active than CDV in vitro against vaccinia, cowpox, ectromelia, variola and monkeypox (Kern, E. R., et al., Antimicrobial Agents Chemotherapy, 46:991-995, 2002; Buller, R. M, et al., Virology, 318:474-481, 2004 and Huggins, J. W., et al., Antiviral Research, 53:A66 (104), 2002). Two of these compounds, hexadecyloxypropyl-CDV (HDP-CDV) and octadecyloxyethyl-CDV (ODE-CDV), are highly protective in various orthopoxvirus lethal challenge models in mice but do not lower viral titers in the lung (Buller, R. M, et al., Virology, 318:474-481, 2004 and Quenelle, D. C., et al., Antimicrobial Agents Chemotherapy, 48:404-412, 2004). Alkoxyalkyl cidofovir analogs are only weakly active in lowering lung viral titers in ectromelia virus infected mice from $3 \times 10^6$ to $10^5$ pfu/gm (Buller, R. M, et al., Virology, 318:474-481, 2004) or not active at all in lowering lung viral titers in cowpox- or vaccinia virus-infected mice (Quenelle, D. C., et al., Antimicrobial Agents Chemotherapy, 48:404-412, 2004). The effect of oral treatment with CDV, HDP-CDV and ODE-CDV on mortality from a lethal aerosol challenge with ectromelia virus has been examined. Four hours after infection, drugs were administered orally for 5 days. Mortality is noted at 21 days. At 7 days a subset of animals was sacrificed and tissues obtained for assessment of viral titers/gm tissue.

| Drug | Mg/kg | Mortality | Liver titer | Spleen titer | Lung titer |
| --- | --- | --- | --- | --- | --- |
| Oral CDV | 10 × 5 d | 100% | $3 \times 10^6$ | $3 \times 10^6$ | $3 \times 10^6$ |
| HDP-CDV | 10 × 5 d | 0% | $<10^2$ | $<10^2$ | $5 \times 10^4$ |
| ODE-CDV | 5 × 5 d | 0% | $<10^2$ | $<10^2$ | $3 \times 10^5$ |

Ectromelia infection, $2.3 \times 10^4$ pfu by small particle aerosol, A/NCR mice; titers pfu/ml (Adapted from Buller, et al. (2004) Virology, 318, 474-481)

This study clearly shows the problem. While both alkoxyalkyl esters, HDP-CDV and ODE-CDV, prevent death from a lethal challenge with ectromelia virus, neither reduced lung viral titers greatly even though viral titers in liver and spleen were below the limit of detection. Similar results were noted in cowpox and vaccinia virus challenge experiments by Quenelle et al. Current alkoxyalkyl conjugates of nucleoside phosphonates and acyclic nucleoside phosphonates do not deliver substantial amounts of drug to lung.

Oral drugs are usually taken up from the small intestine into the portal vein which exposes the drug to the liver and liver first pass drug metabolism which may be very rapid. Very small amounts of the drug administered reach the lung where the infection or lung cancer resides. Therefore, there is a need to develop compounds that target oral antiviral, antifungal, antibacterial or anticancer compounds to the lung.

SUMMARY

Provided herein are compounds and methods for targeted delivery of drugs to lung for treating, preventing, or ameliorating one or more symptoms of diseases or disorders associated with lung diseases, including but not limited to lung infections or lung cancer. In certain embodiments, the compounds provided are conjugates that contain a drug moiety conjugated to a glycerol ether or an analog thereof. The glycerol ether for use herein can be a thio or oxy-alkyl glycerol ether. In certain embodiments, the glycerol ether analog is glycerol phosphate ether. The drug moieties for use herein include antiviral, antimicrobial drugs, antiparasitic or anticancer drugs. Exemplary antimicrobial drugs for use herein include, but are not limited to rifampin, rifamycin and ethambutol. Exemplary antiviral drugs include, but are not limited to, cidofovir (CDV), idoxuridine (IDU), vidarabine (adenine arabinoside, ara-A), trifluridine (trifluorothymidine), acyclovir, famciclovir penciclovir, valacyclovir, ganciclovir, foscarnet, ribavirin, amantadine and rimantadine. Exemplary anticancer drugs for use herein include Carboplatin, Cisplatin, Docetaxel, Etoposide, Gemcitabine, Irinotecan, Paclitaxel, and Vinorelbine. In certain embodiments, the conjugates of antiviral, antimicrobial and anticancer compounds with 1-O-octadecyl-2-O-benzyl-sn-glycerol (ODBG) or 1-O-octadecyl-2-O-benzyl-sn-glycero-3-phosphate (ODBG-P) provided herein are useful for treatment of infections of the lung and lung cancers.

In certain embodiments, the glycerol ether analogs for use herein are sn-glycerol-3-phosphate. In other embodiments, the glycerol ether analogs for use herein are sn-glycerol-1-phosphate ethers. The glycerol alkyl ethers, in certain embodiments, contain up to 24 carbons in the alkyl group. In other embodiments, the sn-1 position of glycerol can contain from 12 up to 24 carbon atoms in the alkyl group. The alkyl group can contain straight or branched chains having 0 to 6 double bonds or other substitutions including halogens, hydroxyl or epoxide. In other embodiments, the sn-2 position of glycerol can contain thio- or oxy-ether substituents selected from aralkyl, such as benzyl or straight or branched alkyl chains 1 to 14 carbons in length which are substituted or unsubstituted with 0 to 2 double bonds.

In certain embodiments, nucleosides for treating viral diseases, antibiotics, antifungal and anticancer drugs can be conjugated to either 1-O-octadecyl-2-O-benzyl-sn-glycerol (linked via the phosphonate) or 1-O-octadecyl-2-O-benzyl-sn-glycero-3-phosphate (linked via the 5' hydroxyl of the sugar moiety or its equivalent). The compounds provided herein are orally available and target the lung for treating lung diseases, including but not limited to viral, bacterial or fungal infections or small cell or non-small cell lung cancers.

Also provided herein are methods of treating, preventing, or ameliorating one or more symptoms of diseases or disorders associated with lung diseases, including but not limited to lung cancer or lung infections by administering the conjugates provided herein.

Articles of manufacture are provided containing packaging material, a compound or composition provided herein which is useful for treating, preventing, or ameliorating one or more symptoms of diseases or disorders associated with lung cancer or lung infections using the compounds and compositions provided herein, and a label that indicates that the compound or composition is useful for treating, preventing, or ameliorating one or more symptoms of diseases or disorders associated with lung cancer or lung infections.

DETAILED DESCRIPTION

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

The singular forms "a," "an," and "the" include plural references, unless the context clearly dictates otherwise. Thus, for example, references to a composition for delivering "a drug" include reference to one, two or more drugs.

As used herein, "drug" or "drug moiety" is any drug or other agent that is intended for delivery to a targeted cell or tissue, such as lungs cells or tissues. Drug moiety for use herein, include, but are not limited to, antiviral, antimicrobial drugs, antiparasitic or anticancer drugs.

As used herein, "linking moiety" or "linker" refers to any moiety that connects the drug moiety and glycerol ether or an analog thereof. The linking moiety can be a covalent bond or a chemical functional group that directly connects the drug moiety to glycerol ether or an analog thereof. The linking moiety can contain a series of covalently bonded atoms and their substituents. Linking moieties are characterized by a first covalent bond or a chemical functional group that connects the drug moiety to a first end of the linker group and a second covalent bond or chemical functional group that connects the second end of the linker group to glycerol ether or an analog thereof.

As used herein "subject" is an animal, typically a mammal, including human, such as a patient.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and inorganic salts, such as but not limited to, sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, mesylates, and fumarates. Pharmaceutically acceptable esters include, but are not limited to, alkyl, alkenyl, alkynyl, aryl, aralkyl and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C═C(OR) where R is hydrogen, alkyl, alkenyl, alkynyl, aryl, aralkyl, cycloalkyl. Pharmaceutically acceptable enol esters include, but are not limited to, derivatives of formula C═C(OC(O)R) where R is hydrogen, alkyl, alkenyl, alkynyl, aryl, aralkyl, or cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392). Other prodrugs for use herein are described elsewhere herein.

As used herein, $EC_{50}$ refers to a dosage, concentration or amount of a particular test compound that elicits a dose-dependent response at 50% of maximal expression of a particular response that is induced, provoked or potentiated by the particular test compound.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. The configuration for naturally occurring amino acid residues is generally L. When not specified the residue is the L form. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

The term "nucleoside" as used herein, refers to a molecule composed of a heterocyclic base and a carbohydrate. Typically, a nucleoside is composed of a heterocyclic nitrogenous base in N-glycosidic linkage with a sugar. Nucleosides are recognized in the art to include natural bases (standard), and non-natural bases well known in the art. The carbohydrates include the true sugars found in natural nucleosides or a species replacing the ribofuranosyl moiety or acyclic sugars. The heterocyclic nitrogenous bases are generally located at the 1' position of a nucleoside sugar moiety. Nucleosides generally contain a base and sugar group. The nucleosides can be unmodified or modified at the sugar, and/or base moiety, (also referred to interchangeably as nucleoside analogs, modified nucleosides, non-natural nucleosides, non-standard nucleosides; see for example, Eckstein et al., International PCT Publication No. WO 92/07065 and Usman et al., International PCT Publication No. WO 93/15187). In natural nucleosides the heterocyclic base is typically thymine, uracil, cytosine, adenine or guanine. The carbohydrate shall be understood to mean the true sugar found in natural nucleosides or a species replacing the ribofuranosyl moiety or acyclic sugars. In certain embodiments, acyclic sugars contain 3-6 carbon atoms and include, for example, the acyclic sugar moieties present in acyclovir (—$CH_2$—O—$CH_2CH_2$—OH), ganciclovir (—$CH_2$—O—CH($CH_2$OH)—$CH_2$—OH), and the like. Natural nucleosides have the β-D-configuration. The term "nucleoside" shall be understood to encompass unnatural configurations and species replacing the true sugar that lack an anomeric carbon. In natural nucleosides the heteocyclic base is attached to the carbohydrate through a carbon-nitrogen bond. The term "nucleoside" shall be understood to encompass species wherein the heterocyclic base and carbohydrate are attached through a carbon-carbon bond (C-nucleosides).

As used herein, the nomenclature alkyl, alkoxy, carbonyl. etc. is used as is generally understood by those of skill in this art.

As used herein, alkyl, alkenyl and alkynyl carbon chains, if not specified, contain from 1 to 20 carbons, or 1 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tort-butyl, isopentyl, neopentyl, tert-pentyl, isohexyl, ethene, propene, butene, pentene, acetylene and hexyne. As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "cycloalkyl" refers to a saturated mono- or multicyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or Spiro-connected fashion. "Cycloalk(en)(yn)yl" refers to a cycloalkyl group containing at least one double bond and at least one triple bond.

As used herein, "substituted alkyl," "substituted alkenyl," "substituted alkynyl," "substituted cycloalkyl," "substituted cycloalkenyl," and "substituted cycloalkynyl" refer to alkyl, alkenyl, alkynyl, cycloalkyl, cycloalkenyl and cycloalkynyl groups, respectively, that are substituted with one or more substituents, in certain embodiments one to three or four substituents, where the substituents are as defined herein, generally selected from Q.

As used herein, "aryl" refers to aromatic monocyclic or multicyclic groups containing from 6 to 19 carbon atoms. Aryl groups include, but are not limited to groups such as fluorenyl, substituted fluorenyl, phenyl, substituted phenyl, naphthyl and substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, tetrazolyl, thienyl, pyridyl, pyrrolyl, N-methylpyrrolyl, quinolinyl and isoquinolinyl.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) Biochem. 11:942-944).

B. Compounds

Provided herein are conjugates of drugs and glycerol ether or analog thereof for use in the methods and compositions for treating lung diseases, including but not limited to lung infections and lung cancer. The drug moiety can be linked to the glycerol ether or analog thereof via a covalent bond or via a hetero bifunctional linker. The conjugates provided herein are not limited to specific drug, linker and glycerol ether moieties. Various combinations of the drugs, linkers and glycerol ether moieties are contemplated. In the conjugates provided herein, the drug moiety is conjugated at 1 or 3 position of glycerol moiety.

In certain embodiments, the conjugates for use herein have the following general formula:

wherein L is a single bond, a phosphate group or a linker;
D is a drug;
X and Y are each independently O or S;
$R_1$ alkyl, alkenyl, alkynyl, optionally substituted with one or more groups selected from Q;
$R_2$ is selected from aralkyl, straight or branched alkyl or alkenyl chains of 1 to 14 carbons, optionally substituted with one or more groups selected Q, where Q is halogen, alkyl, alkenyl, alkynyl, $-OR^w$, $-SR^w$ cycloalkyl or epoxide, where each $R^w$ is independently hydrogen or alkyl and where the alkyl, alkenyl, alkynyl groups may be substituted or unsubstituted.

In certain embodiments, the conjugates for use herein have the following general formula:

wherein L is a single bond, a phosphate group or a linker;
D is a drug;
X and Y are each independently O or S;
$R_1$ is straight or branched chain alkyl or alkenyl of up to 24 carbons, optionally substituted with one or more groups selected from halogen, lower alkyl, hydroxyl or epoxide; and
$R_2$ is selected from aralkyl, straight or branched alkyl or alkenyl chains of 1 to 14 carbons, optionally substituted with one or more groups selected from halogen, lower alkyl, hydroxyl or epoxide.

In certain embodiments, $R_1$ is octadecyl, hexadecyl or myristyl. In certain embodiments, $R_2$ is benzyl, octyl, dodecyl or hexyl.

In certain embodiments, the alkyl ethers at the sn-1 position of glycerol may be thio- or oxy-ethers having 12 to 24 carbons in the alkyl group and may be straight or branched chains having 0 to 6 double bonds. The alkyl groups are optionally substituted with one or more substituents selected from halogens, hydroxyl, alkoxy and epoxide. In other embodiments, at the sn-2 position of glycerol, the thio- or oxy-ether substituents may be aralkyl, including, but not limited to benzyl or straight or branched alkyl chains of 1 to 14 carbons in length which optionally contain one or more double bonds. The alkyl and aralkyl groups at sn-2 position are optionally substituted with one or more substituents selected from halogen, hydroxyl, alkoxy and epoxide groups. The sum of carbon atoms in the ether alkyl groups at the 1 and 2 positions of glycerol may range between 20 and 35, in certain embodiments between 22-30, in certain embodiments between 22-28. In certain embodiments the sum is 20, 21, 22, 23, 24, 25, 26, 27, 28, 29 or 30. In certain embodiments, the $R^2$ group is an alkenyl group and contains 0-2 double bonds.

Without being bound by any theory, in certain embodiments, highly hydrophobic conjugates of cidofovir (CDV) and other drugs may be taken up by the enterocyte, traversing the small intestinal lymphatics with the triglyceride-rich chylomicrons, instead of passing directly into the liver via the portal vein. Intestinal lymphatic lipids (chyle) drain via the thoracic duct successively into the left subclavian vein, innominate vein, superior vena cava, right side of the heart and into the lung via the pulmonary artery. The first tissue reached by the drugs conjugated with 1-O-octadecyl-2-O-benzyl-sn-glycerol (ODBG) or 1-O-octadecyl-2-O-benzyl-sn-glycero-3-phosphate (ODBG-P) will be the lung. In certain embodiments, the drugs are conjugated to ether analogs of sn-glycerol-3-phosphate. In other embodiments, sn-glycerol-1-phosphate ethers are used for conjugation.

The configuration at sn-2 carbon of glycerol may be R or S.

In certain embodiments, the conjugates have formula:

wherein the variables are as defined elsewhere.

In certain embodiments, the compounds have formula

where the variables are as defined elsewhere.

In certain embodiments, X and Y are O. In certain embodiments, X and Y are S.

In certain embodiments, X is O. In certain embodiments, X is S. In certain embodiments, Y is O. In certain embodiments, Y is S.

In certain embodiments, $R_1$ is a straight or branched chain alkyl group. In certain embodiments, $R_1$ is optionally substituted with one or more groups selected from halogen, lower alkyl, hydroxyl or epoxide. In certain embodiments, $R_1$ is substituted with one or more halogen. In certain embodiments, $R_1$ is substituted with one or more lower alkyl. In certain embodiments, $R_1$ is substituted with one or more OH. In certain embodiments, $R_1$ is substituted with one or more epoxide.

In certain embodiments, $R_1$ is alkyl and the alkyl group contains up to 24 carbon atoms. In other embodiments, the alkyl group contains from 12 up to 24 carbon atoms.

In other embodiments, the alkyl group contains 12, 13, 14, 15, 16, 17, 18, 19, 20, 21, 22, 23 or 24 carbon atoms.

In certain embodiments, $R_2$ is selected from aralkyl and straight or branched chain alkyl group. In certain embodiments, $R_2$ is aralkyl group. In certain embodiments, $R_2$ is benzyl group. In other embodiments, $R_2$ is straight or branched chain alkyl group. In certain embodiments, $R_2$ is an alkyl group that contains up to 14 carbon atoms.

In certain embodiments, $R_2$ is a straight or branched chain alkyl group. In certain embodiments, $R_2$ is optionally substituted with one or more groups selected from halogen, lower alkyl, hydroxyl or epoxide. In certain embodiments, $R_2$ is substituted with one or more halogen. In certain embodiments, $R_2$ is substituted with one or more lower alkyl. In certain embodiments, $R_2$ is substituted with one or more OH. In certain embodiments, $R_2$ is substituted with one or more epoxide.

In certain embodiments, $R_1$ and $R_2$ are alkyl groups and the sum of carbon atoms is between 20 and 30. In other embodiments, $R_1$ and $R_2$ are alkyl groups and the sum of carbon atoms is between 22 and 28. In other embodiments, $R_1$ and $R_2$ are alkyl groups and the sum of carbon atoms is 22, 23, 24, 25, 26, 27 or 28.

Glycerols

In certain embodiments, the drug is conjugated to the glycerol at 3 position. In other embodiments, the glycerol for use in the conjugates provided herein is 1-O-alkyl-glycerol. In certain embodiments, the glycerol is selected from 1-O-octadecyl-2-O-benzyl-sn-glycerol (ODBG), 1-O-hexadecyl-2-O-octyl-sn-glycerol, 1-S-hexadecyl-2-O-octyl-sn-thioglycerol, 1-S-myristyl-2-O-dodecyl-sn-thioglycerol, 1-O-myristyl-2-S-dodecyl-sn-thioglycerol, 1-O-hexadecyl-2-O-hexyl-sn-glycerol, 1-O-octadecyl-2-O-octyl-sn-glycerol and glycerol phosphate analog thereof. In certain embodiments, the glycerol phosphate for use herein includes 1-O-octadecyl-2-O-benzyl-sn-glycero-3-phosphate (ODBG-P).

Linkers

In certain embodiments, the conjugates optionally contain a linker that covalently binds the glycerol ether to the drug moiety. In certain embodiments, the linker can include carbohydrate, peptide, diamine, arylamine, and/or hydrocarbon core structures. The linkers are, in certain embodiments, synthetically accessible, provide shelf-stable products, and do not possess any intrinsic biological activity that interferes with the conjugates activity. They can add desirable properties such as increasing solubility. A variety of linking moieties are known to those of skill in the art, which may be used in the conjugates provided herein. Any bifunctional linker, in certain embodiments, heterobifunctional linker that can form a bond between the drug moiety and the glycerol ether, when incorporated in the conjugate, can be used in the conjugates provided herein.

Examples of functional groups on the linker include —$NH_2$, —$NHNH_2$, —$ONH_2$, —NHC=(O)$NHNH_2$, —OH, —CHO, halogen, —$CO_2H$, and —SH. Each of these functional groups can form a covalent linkage to a suitable functional group on the drug moiety or the glycerol ether moiety in the conjugates provided herein. For example, amino, hydroxy and hydrazino groups can each form a covalent bond with a reactive carboxyl group (e.g., a carboxylic acid chloride or activated ester such as an N-hydroxysuccinimide ester (NHS)). Other suitable bond forming groups are well-known in the literature. The linking moiety can include linear or acyclic portions, cyclic portions, aromatic rings or combinations thereof.

In certain embodiments, the hydroxyl group of alkyl glycerol ether is conjugated, optionally via a linker to a phosphonate group of a drug moiety. In other embodiments, a phosphate group on the alkyl glycerol is conjugated, to a suitable functional group on the drug moiety.

Drugs

Analogs of CDV and other antiviral acyclic nucleoside phosphonates such as (S)-9-[3-hydroxy-2-(phosphonomethoxy)propyl]adenine ((S)-HPMPA) and phosphonomethoxyethylguanine (PMEG) which provide higher drug levels in lung after oral administration could lower the titers of poxvirus and other viruses in lung. The following list of patents describe acyclic nucleoside phosphonates which are subject compounds herein when modified by conjugation to 1-O-octadecyl-2-O-benzyl-sn-glycerol and other glycerol ethers described herein. The patents in this list are hereby incorporated by reference in their entirety.

| Document ID | Title | Inventor (first) |
|---|---|---|
| CZ 292199 | O-Phosphonomethyl Choline and Alkyl Esters thereof, process of their preparation and use | Holy, A. (anti-cancer agents) |
| U.S. Pat. No. 6,653,296<br>U.S. Pat. No. 6,057,305 | Preparation of Anti-retroviral Enantiomeric nucleotide Analogs | Holy, A. (tenofovir, PMPA) |
| U.S. Pat. No. 5,977,061 | Acyclic Nucleosides as Virucides and Immunostimulation Suppressants | Holy, A. (HPMPDAP) |
| U.S. Pat. No. 5,733,896 | Preparation of N-(3-fluoro-2-phosphonylmethoxypropyl)purines and -pyrimidines as antiviral agents | Holy, A. |
| CZ 263953 | Method for the Preparation of 9-(S)- and 9-(R,S)-(3-hydroxy-2-phosphonylmethoxypropyl)adenine as virucides | Holy, A. |
| CZ 263955 | Method for the preparation of N-[3-hydroxy-2-(phosphonylmethoxy)propyl]purines and -pyrimidines | Holy, A. |
| CZ 263956 | Method for the preparation of virucidal 9-(S)-(3-hydroxy-2-phosphonylmethoxypropyl)adenine | Holy, A. |

-continued

| Document ID | Title | Inventor (first) |
|---|---|---|
| U.S. Pat. No. 5,641,763 | Preparation and testing of N-phosphonylmethoxyalkyl derivatives of pyrimidine and purine bases with antiviral activity | Holy, A. (excludes HPMPA, includes PMEG) |
| U.S. Pat. No. 5,869,467 | | |
| U.S. Pat. No. 4,808,716 | Preparation of 9-[phosphonomethoxy)alkyl]adenines and their use as virucides | Holy, A. (HPMPA) |
| U.S. Pat. No. 4,724,233 | Use of phosphonylmethoxyalkyladenines in the treatment of virus diseases | De Clerq, E. |
| FR 2539132 | Isomeric O-phosphonylmethyl derivatives of enantiomeric and racemic vicinal diols | Holy, A. |
| WO 2004096286 | Preparation of phosphonate prodrugs of antiviral compounds | Boojamara, C. G. |
| US 2004023928 | Phosphonate nucleotide and thiadiazole compounds for the treatment of smallpox | Colacino, J. M. |
| US 2004023921 | Antiviral Phosphonate Nucleotide Analogs | Hong, Z. |
| WO 2003099294 | Improvement in drug selectivity of targeting tissues for therapeutic efficiency | Ubasawa, K. |
| WO 2003090691 | Preparation of phosphonate analogs of HIV protease inhibitors and methods for identifying anti-HIV therapeutic compounds | Birkus, G. |
| WO 2003090690 | Preparation of phosphonate analogs of HIV protease inhibitors with improved cellular accumulation properties | Arimilli, M. N. |
| WO 2003050129 | Use of phosphonate nucleotide analog LY582563 for treating hepatitis B virus infections | Wise, S. D. |
| US 2003109498 | 2-Amino-6-arylthiopurine phosphonate antiviral agents for treatment of drug-resistant virus infections | Yuasa, S. |
| RU 2187509 | Preparation of derivatives of 3-azido-3-deoxythymidine 5'-H-phosphonates as antiviral agents | Shirokova, E. A. |
| WO 2003002580 | Preparation of phosphonate-substituted pyrimidine analogs as antiviral agents | Balzarini, J. M. (DAPy) |
| U.S. Pat. No. 644656 | Preparation of antiviral phosphonate nucleotides | Nguyen-Ba, Nghe |
| U.S. Pat. No. 5,955,610 | | |
| U.S. Pat. No. 6,005,107 | | |
| U.S. Pat. No. 6,127,540 | | |
| WO 2002057288 | Preparation of acyclic nucleoside phosphonates as antiviral agents against hepatitis B virius | Choi, J-R. |
| WO 2001064693 | Preparation of phosphonate nucleotide compounds as antiviral agents | Ubasawa, M. |
| WO 2000029414 | Preparation of dialkyl 1-aryl-1-[(2,4-dioxo-1,3-pyrimidin-5-yl)amino]methylphosphonates as antiviral and antimicrobial agents | Tets, V. |
| WO 9962921 | Preparation of antiviral phosphorous derivatives of 4-thio-5-ethyl-2-deoxyuridine | Alexandrovna, A. |
| U.S. Pat. No. 5,886,179 | Preparation of nucleotide phosphonate ester analogs as antiviral agents | Arimilli, M. N. |
| U.S. Pat. No. 5,656,745 | | |
| WO 9319075 | Preparation of purine-substituted phosphonates as antiviral agents | Harnden, M. R. |
| U.S. Pat. No. 5,817,647 | Unsaturated phosphonate derivatives of purines and pyrimidines | Casara, P. |
| U.S. Pat. No. 5,922,696 | | |
| U.S. Pat. No. 5,532,225 | Preparation of acyclic purine phosphonate nucleotide analogs as antiviral agents | Reist, E. J. |
| U.S. Pat. No. 5,877,166 | Preparation of enantiomerically pure 2-aminopurine phosphonate nucleotide analogs as antiviral agents | Reist, E. J. |

-continued

| Document ID | Title | Inventor (first) |
| --- | --- | --- |
| WO 9842351 | Preparation of difluoronucleoside phosphonic acids as antiviral and antineoplastic agents | Hertel, L. W. |
| WO 9838202 | Preparation of nucleoside phosphonates as antivirals | Rosowsky, A. |
| U.S. Pat. No. 5,717,095 | Preparation of cyclic nucleotide phosphonate esters as virucides | Arimilli, M. N. |
| U.S. Pat. No. 5,650,510 | Antiviral | Webb, R. R. |
| U.S. Pat. No. 5,854,228 | phosphonomethoxyalkylpurines and —pyrimidines and their preparation | (PMEG) |
| U.S. Pat. No. 5,840,716 | Preparation of acyclic nucleotide phosphonates as virucides | Ubasawa, M. |
| U.S. Pat. No. 5,798,340 U.S. Pat. No. 6,225,460 | Preparation of virucidal nucleotide analogs | Bischofberger, N. W. |
| U.S. Pat. No. 6,197,775 | Preparartion of phosphonate acyclic nucleotide derivatives as antiviral agents | Ubasawa, M. |

Antimicrobial agents against tuberculosis may also be conjugated to glycerol ethers or analogs thereof as described herein. Such antimicrobial agents include rifampin, rifamycin and ethambutol which may be coupled to 1-O-octadecyl-2-O-benzyl-sn-glycerol-3-phosphate or other glycerol phosphate ethers provided herein by linking to one of their available hydroxyl groups. Isoniazid may be coupled to 1-O-octadecyl-2-O-benzyl-sn-glycerol-3-phosphate or other glycerol phosphate ethers described herein using a bifunctional linker such as 3-hydroxypropanoic acid. Antiviral agents against influenza virus infections may be similarly prepared by linking 1-O-octadecyl-2-O-benzyl-sn-glycerol-3-phosphate or other glycerol phosphate ethers described herein to an available hydroxyl of zanamavir (Relenza®) or to other influenza drugs. Other influenza drugs include neuraminidase inhibitors, including those disclosed in Chand, P. (2005) Expert Opinion on Therapeutic Patents, 15(8), 1009-1025; U.S. Pat. No. 6,562,861 (peramivir); and U.S. Pat. No. 6,455,571 (A-315675).

Lung cancer nucleoside agents may also be derivatized as described herein. Subject compounds which are reported to be active against small cell or non-small cell lung cancer include: 2'-Deoxy-2',2'-difluorocytidine (gemcitabine), (E)-2-deoxy-2-fluoromethylene-cytidine (FMdC), or 1-(2-deoxy-2-fluoro-4-thio-β-D-arabinosyl)cytosine (4-thio-FAC). Other antiproliferative nucleosides which are not generally used against lung cancers may also become active when derivatized with glycerol ethers including: cytosine arabinoside (Ara-C, cytarabine), arabinosylguanine (Ara-G), 5-fluorouridine, 5-fluoro-deoxyuridine, (R)-deoxycoformycin, and fludarabine.

Non-nucleoside lung cancer agents may be similarly derivatized as described herein. Topotecan may be coupled to 1-O-octadecyl-2-O-benzyl-sn-glycerol-3-phosphate or other glycerol phosphate ethers of the invention by coupling to topotecan's available hydroxyl. Etoposide may be coupled to 1-O-octadecyl-2-O-benzyl-sn-glycerol or other glycerol ethers described herein by attachment to the phosphate residue of etoposide.

C. Pharmaceutical Compositions And Dosage Forms

Pharmaceutical compositions and dosage forms for use in the methods provided herein contain a compound provided herein in a pharmaceutically acceptable carrier and in amounts that are useful in the methods provided herein. Such methods include treatment of lung infections and lung cancers.

The compounds provided for use herein are formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the formulations are prepared using techniques and procedures well known in the art (see, e.g., Ansel Introduction to Pharmaceutical Dosage Forms, Seventh Edition 1999).

In the compositions, effective concentrations of a compound provided herein is (are) mixed with a suitable pharmaceutical carrier or vehicle. The concentration of the compound provided herein in the compositions are effective for delivery of an amount, upon administration, that treats, prevents, or ameliorates one or more of the symptoms of conditions associated with lung infections and lung cancers.

Typically, the compositions are formulated for single dosage administration. To formulate a composition, the weight fraction of a compound provided herein is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, a compound provided herein may be formulated as a sole pharmaceutically active ingredient in the composition or may be combined with other active ingredients. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. Nos. 4,522,811; 5,571,534. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

A compound provided herein is included in the pharmaceutically acceptable carrier in an amount sufficient to exert desired effect in the patient treated. The therapeutically effective concentration may be determined empirically by testing a compound provided herein in in vitro and in vivo systems known to one of skill in the art and then extrapolated therefrom for dosages for humans.

The concentration of a compound provided herein in the pharmaceutical composition will depend on absorption, inactivation and excretion rates of a compound provided herein, the dosage schedule, and amount administered as well as other factors known to those of skill in the art.

The composition, shape, and type of dosage forms provided herein will typically vary depending on their use. For example, a dosage form used in the acute treatment of a disease may contain larger amounts of one or more of the active ingredients it contains than a dosage form used in the chronic treatment of the same disease. Similarly, a parenteral dosage form may contain smaller amounts of one or more of the active ingredients it contains than an oral dosage form used to treat the same disease. These and other ways in which specific dosage forms provided herein will vary from one another will be readily apparent to those skilled in the art. See, e.g., *Remington's Pharmaceutical Sciences,* 20th ed., Mack Publishing, Easton Pa. (2000).

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the compositions provided herein.

Thus, effective concentrations or amount of a compound provided herein is mixed with a suitable pharmaceutical carrier or vehicle for systemic, topical or local administration to form the pharmaceutical composition. A compound provided herein is included in an amount effective for treatment of lung infections and lung cancers.

The compositions are intended to be administered by a suitable route, including orally, parenterally, rectally, topically and locally. A compound provided herein is typically formulated and administered in unit-dosage forms such as tablets, capsules, pills, powders, granules, sterile parenteral solutions or suspensions, and oral solutions or suspensions, and oil-water emulsions containing suitable quantities of the active ingredient or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Lactose-free compositions provided herein can contain excipients that are well known in the art and are listed, for example, in the U.S. Pharmacopeia (USP) 25-NF20 (2002). In general, lactose-free compositions contains active ingredients, a binder/filler, and a lubricant in pharmaceutically compatible and pharmaceutically acceptable amounts. Particular lactose-free dosage forms contain active ingredients, microcrystalline cellulose, pre-gelatinized starch, and magnesium stearate.

Further provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

a. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art. Such dosage forms contain predetermined amounts of active ingredients, and may be prepared by methods of pharmacy well known to those skilled in the art. See generally, *Remington's Pharmaceutical Sciences,* 20th ed., Mack Publishing, Easton Pa. (2000).

In certain embodiments, the formulations are solid dosage forms, preferably capsules or tablets. The tablets, pills, capsules, troches and the like can contain any of the following ingredients, or compounds of a similar nature: a binder, a filler, a diluent; a disintegrating agent, a lubricant, a glidant, a sweetening agent, and a flavoring agent. Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103, AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103 and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions herein is typically present in from about 50 to about 99 weight percent of the pharmaceutical composition or dosage form.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions contain from about 0.5 to about 15 weight percent of disintegrant, preferably from about 1 to about 5 weight percent of disintegrant.

Disintegrants that can be used in pharmaceutical compositions and dosage forms provided herein include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL®200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

If oral administration is desired, a compound provided herein could be provided in a composition that is formulated as enteric coating tablets, sugar-coated tablets, film-coated tablets or multiple compressed tablets. Enteric coating tablets protect the active ingredient from the acidic environment of the stomach. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges. The composition may also be formulated in combination with an antacid or other such ingredient.

When the dosage unit form is a capsule, it can contain, in addition to material of the above type, a liquid carrier such as a fatty oil. In a gelatin capsule, the solution or suspension containing a compound provided herein, in for example propylene carbonate, vegetable oils or triglycerides, is preferably encapsulated in the capsule. Such solutions, and the preparation and encapsulation thereof, are disclosed in U.S. Pat. Nos. 4,328,245; 4,409,239; and 4,410,545.

The active ingredient can also be mixed with other active materials which do not impair the desired action, or with materials that supplement the desired action, such as antacids, H2 blockers, and diuretics. Higher concentrations, up to about 98% by weight of the active ingredient may be included.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative.

An emulsion is a two-phase system in which one liquid is dispersed in the form of small globules throughout another liquid. Pharmaceutically acceptable carriers used in emulsions are non-aqueous liquids, emulsifying agents and preservatives.

Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia.

Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

The pharmaceutical compositions containing active ingredients in micellar form can be prepared as described in U.S.

Pat. No. 6,350,458. Such pharmaceutical compositions are particularly effective in oral, nasal and buccal applications.

In certain embodiments, formulations include, but are not limited to, those containing a compound provided herein, a dialkylated mono- or poly-alkynyl glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

b. Controlled Release Dosage Form

Active ingredients provided herein can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321: 574 (1989). In another embodiment, polymeric materials can be used. In yet another embodiment, a controlled release system can be placed in proximity of the therapeutic target, i.e., thus requiring only a fraction of the systemic dose (see, e.g., Goodson, *Medical Applications of Controlled Release*, vol. 2, pp. 115-138 (1984).

Preferably, a controlled release device is introduced into a subject in proximity of the site of inappropriate immune activation or a tumor. Other controlled release systems are discussed in the review by Langer (*Science* 249:1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

c. Parenteral Administration

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of a compound provided herein is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active ingredient is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of a compound provided herein to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

A compound provided herein may be suspended in micronized or other suitable form or may be derivatized to produce a more soluble active product or to produce a prodrug. The form of the resulting mixture depends upon a number of factors, including the intended mode of administration and the solubility of a compound provided herein in the selected carrier or vehicle. The effective concentration is sufficient for ameliorating the symptoms of the condition and may be empirically determined.

d. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving the active ingredient, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-500 mg, preferably 100-300 mg) or multiple dosages of a compound provided herein. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

e. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds provided herein may be formulated for local or topical application, such as for topical application to the skin and mucous membranes, in the form of gels, creams, and lotions. Topical administration is contemplated for transdermal delivery and also for administration mucosa, or for inhalation therapies.

g. Articles of Manufacture

The compounds provided herein may be packaged as articles of manufacture containing packaging material and a label that indicates that the compound is used for treatment of lung infections and lung cancers. The articles of manufacture provided herein contain packaging materials.

Packaging materials for use in packaging pharmaceutical products are well known to those of skill in the art. See, e.g., U.S. Pat. Nos. 5,323,907, 5,052,558 and 5,033,352. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds provided herein are contemplated herein.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

Example 1

Synthesis of 1-O-Octadecyl-2-O-benzyl-sn-glycero-3-cidofovir (ODBC-CDV)

ODBG-CDV was synthesized as shown in Scheme 1. A mixture of cyclic cidofovir (Bischofberger, et al. (1994) Antimicrob. Agents Chemo., 38(10), 2387-2391), 1-O-octadecyl-2-O-benzyl-sn-glycerol (Bachem, Torrance, Calif.) and triphenylphosphine was treated with diisopropylazodicarboxylate (Mitsunobu reaction) (Saady, et al. (1995) Syn. Lett., (6), 643-644) to give the cyclic ester. Base catalyzed hydrolysis gave ODBG-CDV as the sodium salt.

Scheme 1. Synthesis of ODBG-CDV.

Reagents: a) triphenylphosphine, diisopropylazodicarboxylate, N,N-DMF; b) 1 N NaOH, 40° C.

By substituting other glycerol ether analogs for 1-O-octadecyl-2-O-benzyl-sn-glycerol, other compounds provided herein can be prepared. For example, 1-O-hexadecyl-2-O-octyl-sn-glycerol, 1-S-hexadecyl-2-O-octyl-sn-thioglycerol, 1-S-myristyl-2-O-dodecyl-sn-thioglycerol, 1-O-myristyl-2-S-dodecyl-sn-thioglycerol, 1-O-hexadecyl-2-O-hexyl-sn-glycerol, 1-O-octadecyl-2-O-octyl-sn-glycerol adducts of cyclic CDV followed by ring opening give the corresponding CDV adduct.

Example 2

Synthesis of 1-O-Octadecyl-2-O-benzyl-sn-glycero-3-(S)-HPMPA (ODBG-(S)—HPMPA)

(S)-HPMPA derivatives are converted to ODBG-(S)-HPMPA as follows.
Toluenesulfonyloxymethyl-phosphonic acid is first esterified with 1-O-octadecyl-2-O-benzyl-sn-glycerol to give ODBG-TsOMPA.

Scheme 2. Synthesis of ODBG-(S)-HPMPA.

ODBG-TsOMPA

ODBG-(S)-HPMPA

Reagents: a) NaH, N,N-DMF; b) 80% aq acetic acid, 60° C. (Jasko, et al. (1994) Bioorgan. Khimiya, 20(1), 50-54).

Reaction of ODBG-TsOMPA with $O^{3'}$, $N^6$-ditrityl-(S)-dihydroxypropyladenine in the presence of sodium hydride will give the fully protected HPMPA ester (Webb (1989) Nucleosides & Nucleotides, 8(4), 619-624). Removal of the trityl blocking groups (80% aq acetic acid) yields ODBG-(S)-HPMPA.

Alternatively, ODBG-(S)-HPMPA could be synthesized using a process analogous to that described in Example 1. A mixture of cyclic (S)-HPMPA (Rosenberg, I. and Holy, A (1987) Collection of Czechoslovak Chemical Communications, 52(11), 2792-2800), 1-O-octadecyl-2-O-benzyl-sn-glycerol (Bachem, Torrance Calif.) and triphenylphosphine was treated with diisopropylazodicarboxylate to give ODBG-(S)-cyclic HPMPA. Base catalyzed hydrolysis yielded ODBG-(S)-HPMPA.

By substituting other glycerol ether analogs for 1-O-octadecyl-2-O-benzyl-sn-glycerol, other compounds provided herein can be prepared. For example, the 1-O-hexadecyl-2-O-octyl-sn-glycerol, 1-S-hexadecyl-2-O-octyl-sn-thioglycerol, 1-S-myristyl-2-O-dodecyl-sn-thioglycerol, 1-O-myristyl-2-S-dodecyl-sn-thioglycerol, 1-O-hexadecyl-2-O-hexyl-sn-glycerol, 1-O-octadecyl-2-O-octyl-sn-glycerol adducts of (S)HPMPA can be prepared using similar procedure.

Example 3

Synthesis of 1-O-Octadecyl-2-O-benzyl-sn-glycero-3-PMEG (ODBG-PMEG)

ODBG-PMEG is prepared as shown in Scheme 3. ODBG and 9-[(phosphonylmethoxy)ethyl]-2-amino-6-chloropurine are coupled by treatment with N,N-dicyclohexylcarbodiimide (DCC). Subsequent acidic hydrolysis gives the desired PMEG ester.

Scheme 3. Synthesis of ODBG-PMEG.

ODBG

ODBG-PMEG

Reagents: a) DCC, pyridine, N,N-DMF; b) 1M HCl, reflux.

By substituting other glycerol ether analogs for 1-O-octadecyl-2-O-benzyl-sn-glycerol, other compounds provided herein may be prepared. For example, 1-O-hexadecyl-2-O-octyl-sn-glycerol, 1-S-hexadecyl-2-O-octyl-sn-thioglycerol, 1-S-myristyl-2-O-dodecyl-sn-thioglycerol, 1-O-myristyl-2-S-dodecyl-sn-thioglycerol, 1-O-hexadecyl-2-O-hexyl-sn-glycerol, 1-O-octadecyl-2-O-octyl-sn-glycerol adducts of PMEG can be prepared similarly.

Example 4

Synthesis of 1-O-octadecyl-2-O-benzyl-sn-glycero-3-gemcitibine (2'-Deoxy-2',2'-difluorocytidine)

To a solution of 2'-Deoxy-2',2'-difluorocytidine (260 mg, 1 mmol) and 1-O-octadecyl-2-O-benzyl-sn-glycero-3-phosphate (515 mg, 1 mmol) in dry pyridine (20 mL) was added dicyclohexylcarbodiimide (DCC, 618 mg, 3 mmol). The mixture was stirred and heated to reflux and kept 5 hours. After cooling, the mixture was filtered and the filtrate was evaporated in vacuo. The residue was applied to column of silica gel and eluted with 10% MeOH/90% $CH_2Cl_2$ to give gemcitabine 5'-monophosphate, 1-O-octadecyl-2-O-benzyl-sn-glyceryl ester (ODBG-P-DDFC, 350 mg, 45% yield) as a white powder.

By substituting other glycerol phosphate ether analogs for 1-O-octadecyl-2-O-benzyl-sn-glycerol-3-phosphate, other compounds provided herein can be prepared. For example, the 1-O-hexadecyl-2-O-octyl-sn-glycerol, 1-S-hexadecyl-2-O-octyl-sn-thioglycerol, 1-S-myristoyl-2-O-dodecyl-sn-thioglycerol, 1-O-myristoyl-2-S-dodecyl-sn-thioglycerol, 1-O-hexadecyl-2-O-hexyl-sn-glycerol, 1-O-octadecyl-2-O- octyl-sn-glycerol adducts of other anti-lung cancer nucleosides such as (E)-2-deoxy-2-fluoromethylene-cytidine (FMdC), or 1-(2-deoxy-2-fluoro-4-thio-β-D-arabinosyl)cytosine (4-thio-FAC) can be similarly prepared. Other antiproliferative nucleosides which are not in use against lung cancers can become active when derivatized as shown in Example 4 including, Ara-C, Ara-G, 5-fluorouridine, 5-fluoro-deoxyuridine, or fludarabine. Other lung cancer agents may be similarly derivatized with 1-O-octadecyl-2-O-benzyl-sn-glycerol-3-phosphate including topotecan by coupling to an available hydroxyl. Etoposide may be coupled to 1-O-octadecyl-2-O-benzyl-sn-glycerol by attachment to the phosphate residue of etoposide for lung targeted delivery. Antiviral nucleosides active against SARS virus may be coupled via their 5'-hydroxyl (or its equivalent) to 1-O-octadecyl-2-O-benzyl-sn-glycerol-3-phosphate or other glycerol phosphate ethers provided herein.

Example 5

Antiviral Activity of the Lung-Targeted Versus Non-Lung Targeted CDV Derivatives A series of CDV analogs were evaluated against vaccinia and cowpox comparing different linker and alkyl chains. Results are shown in Table 2 comparing the lung targeted analog, ODBG-CDV, with conventional HDP-CDV and ODE-CDV in vaccinia or cowpox-infected cells.

| In vitro Antiviral Activity of CDV Alkoxyalkyl or Alkoxyglycerol Esters | | | | | | |
|---|---|---|---|---|---|---|
| Compound | Lung-targeted | Vaccinia Copenhagen | | | Cowpox Brighton | |
| | | $TC_{50}$, μM | $EC_{50}$, μM | SI | $EC_{50}$, μM | SI |
| CDV | no | >317 | 31 | >10 | 42 | >7.5 |
| HDP-CDV | no | 29 | 0.6 | 48 | 0.5 | 58 |
| ODE-CDV | no | 21 | 0.6 | 105 | 0.5 | 105 |
| ODBG-CDV | yes | 47 | 0.4 | 118 | 0.3 | 157 |

SI = selectivity index ($TC_{50}/EC_{50}$);
references: Keith, et al. (2004) Antimicrob. Agents Chemo., 48, 1869-1871; Keith, et al. (2003) Proc. 16th Internat. Conf. Antiviral Res., #110; and Quenelle et al., (2004) Antimicrob Agents Chemother., 48(2), 404-12 (Erratum in: (2004) Antimicrob Agents Chemother., 48(5), 1919);
$TC_{50}$, toxic dose 50%,
$EC_{50}$, effective dose 50%

ODBG-CDV is equivalent in activity to HDP-CDV and ODE-CDV, the non lung-targeted compounds. Since the $TC_{50}$ is higher, 47 versus 21-29 μM, the selectivity indexes for ODBG-CDV are more favorable against vaccinia and cowpox.

Example 6

Oral Pharmacokinetics of $^{14}$C-Labeled ODBG-CDV versus HDP- and ODE-CDV

Figure 1:
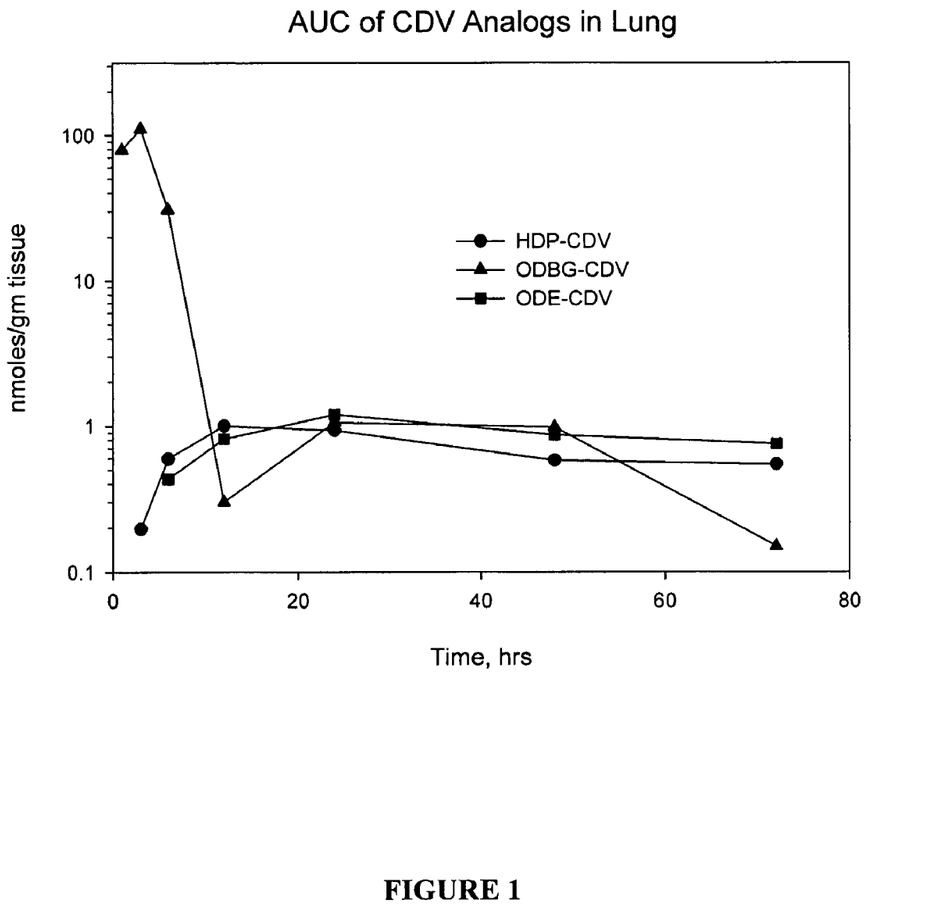
FIG. 1 shows lung levels of $^{14}$C-labeled ODBG-CDV, HDP-CDV and ODE-CDV.
Figure 2:
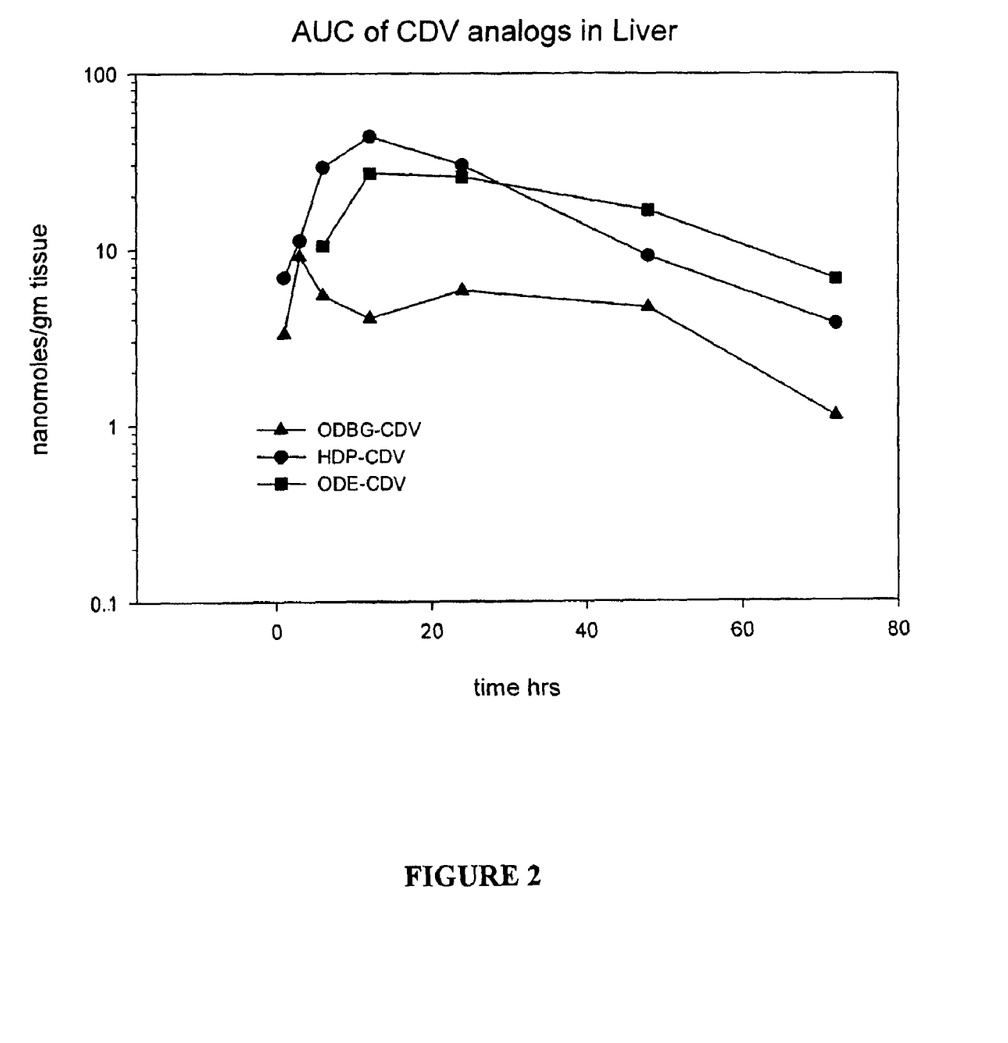
FIG. 2 shows liver levels of $^{14}$C-labeled ODBG-CDV, HDP-CDV and ODE-CDV.

Synthesis, metabolism and pharmacokinetics of ODBG-[2-$^{14}$C]CDV: 1-O-octadecyl-2-O-benzyl-sn-glycerol was purchased from Bachem and provided to Moravek Biochemicals (Brea, Calif.). Using the procedure shown in Example 1, ODBG was coupled to cyclic CDV[2-$^{14}$C]. The ring was opened with NaOH to give ODBG-CDV, sodium salt. This material was used to study cell uptake, metabolism and pharmacokinetics of ODBG-CDV. 10 mg/kg of ODBG-CDV, HDP-CDV or ODE-CDV was given orally to mice and liver and lung levels of CDV equivalents were measured over a period of 72 hours. Data expressed as nmole equivalents of CDV/gm tissue is shown in FIGS. 1 and 2. Lung levels of $^{14}$C-labeled drug were much higher with ODBG-CDV than with HDP-CDV or ODE-CDV (FIG. 1). In contrast, liver levels with ODBG-CDV are lower (FIG. 2).

Area under curve (AUC) values were calculated from FIGS. 1 and 2. HDP-CDV and ODE-CDV given orally result in large AUC in liver and small AUC in lung. Liver AUC values are 20 to 28 times greater than that of lung. However, when ODBG-CDV is given orally, the AUC in lung is larger than AUC in liver as shown below. This is a complete reversal of drug distribution from principally liver to principally lung. This suggests that lung viral titers may be reduced more effectively with ODBG-CDV than with HDP- or ODE-CDV

| Effect of CDV Analog Lipid Structure on Liver and Lung Area Under Curve | | | | |
|---|---|---|---|---|
| Compound | AUC $^{14}$C-Drug (nmol · gm · hrs) | | Ratio | Ratio |
| | Liver | Lung | Lung/Liver | Liver/Lung |
| HDP-CDV | 1367 | 49 | 0.04 | 27.9 |
| ODE-CDV | 1215 | 60 | 0.05 | 20.3 |
| ODBG-CDV | 318 | 581 | 1.82 | 0.55 |

10 mg/kg single oral dose of HDP-, ODE- or ODBG-[2-$^{14}$C]CDV.
AUC, area under curve
0 to 72 hours, expressed as nanomole drug.gm.hrs (Cielsa, et al. (2003) Antiviral Res., 59, 163-171)

1-O-octadecyl-2-O-benzyl-sn-glycero-3-CDV (ODBG-CDV), when given orally, delivers drug to the lung. CDV itself is not orally bioavailable (<6%) and the lung area under curve values are 10-fold greater than the alkoxyalkyl derivatives of CDV which are not lung-targeted. ODBG-CDV is highly active against vaccinia and cowpox viruses in vitro and has antiviral activity equivalent to hexadecyloxypropyl-CDV, a non-lung targeted compound (8). Other poxvirus antivirals such as (S)-HPMPA and phosphonomethoxyethylguanine (PMEG) are also active against orthopoxviruses and may be subjected to the same derivatization to obtain lung-targeted antivirals.

Example 7

Data for ODBG-CDV in Lethal Ectromelia Infection of Mice

Female A/NCR mice were infected intranasally with 30,000 LD50s of ectromelia virus and 4 hours later were treated orally daily for 5 days with water (placebo) or with ODBG-CDV as indicated.

TABLE 1

| Effect of oral ODBG-CDV on ectromelia infection in mice, in vivo | | | |
|---|---|---|---|
| Treatment | Dose | Mortality day 21 | Mean time to death |
| Placebo | water | 10/10 | 7.4 ± 0.5 |
| ODBG-CDV | 2 mg/kg/d | 2/10 | 13.0 ± 1.4 |
| ODBG-CDV | 8 mg/kg/d | 0/10 | n/a |

Tissue homogenates were titered and data are the geometric mean of 5 animals sacrificed 6 days after infection.

TABLE 2

| Ectromelia viral titers in tissue homogenates | | | | |
|---|---|---|---|---|
| Treatment | Dose | Lung | Liver | Spleen |
| Placebo | water | 1,098,000 | 12,006,000 | 13,621,000 |
| ODBG-CDV | 2 mg/kg/d | 254,000 | 16,400 | 1,277,000 |
| ODBG-CDV | 8 mg/kg/d | 27,400 | <100 | 850 |

Results:

1. Oral ODBG-CDV provides protection from death from overwhelming ectromelia infection (30,000 LD50s) in mice (Table 1).
2. ODBG-CDV lowers viral titers in lung from 1,098,000 to 254,000 (2 mg/kg/day×5 days) and 27,400 (8 mg/kg/day×5 days). (Table 2).

Since modifications will be apparent to those of skill in this art, it is intended that this invention be limited only by the scope of the appended claims.

What is claimed is:

1. A compound having the structure or pharmaceutically acceptable salt thereof.

2. A compound having the structure or pharmaceutically acceptable salt thereof.

3. A compound having the structure or pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,101,745 B2 | |
| APPLICATION NO. | : 11/793276 | |
| DATED | : January 24, 2012 | |
| INVENTOR(S) | : Karl Y. Hostetler et al. | |

It is certified that error appears in the above-identified patent and that said Letters Patent is hereby corrected as shown below:

In the Claims:

In column 30, claim 3, line 25, at left, delete "BzO" and insert --BnO--.

Signed and Sealed this
Twenty-ninth Day of May, 2012

David J. Kappos
*Director of the United States Patent and Trademark Office*